(12) United States Patent
Hovorka

(10) Patent No.: US 8,977,504 B2
(45) Date of Patent: Mar. 10, 2015

(54) SUBSTANCE MONITORING AND CONTROL IN HUMAN OR ANIMAL BODIES

(75) Inventor: Roman Hovorka, Cambridgeshire (GB)

(73) Assignee: Cambridge Enterprise Limited, Cambridgeshire (GB)

( * ) Notice: Subject to any disclaimer, the term of this patent is extended or adjusted under 35 U.S.C. 154(b) by 1001 days.

(21) Appl. No.: 12/682,543

(22) PCT Filed: Oct. 10, 2008

(86) PCT No.: PCT/GB2008/050932
§ 371 (c)(1),
(2), (4) Date: Aug. 24, 2010

(87) PCT Pub. No.: WO2009/047569
PCT Pub. Date: Apr. 16, 2009

(65) Prior Publication Data
US 2011/0040487 A1     Feb. 17, 2011

(30) Foreign Application Priority Data

Oct. 12, 2007     (GB) .................................. 0719969.8

(51) Int. Cl.
*G01N 33/48*     (2006.01)
*G01N 31/00*     (2006.01)
(Continued)

(52) U.S. Cl.
CPC ........ *G06F 19/3437* (2013.01); *G06F 19/3456* (2013.01)
USPC ................... 702/19; 702/22; 703/11; 703/12

(58) Field of Classification Search
CPC . G06F 19/36; G06F 19/3437; G06F 19/3456; G06F 19/3481; A61B 5/14532; A61B 5/7275; A61M 2005/14208
See application file for complete search history.

(56) References Cited

U.S. PATENT DOCUMENTS 4,055,175 A     10/1977 Clemens et al.
4,464,170 A     8/1984 Clemens et al.
(Continued)

FOREIGN PATENT DOCUMENTS

EP     1 278 564 B1     7/2006
GB     2 436 873 A     10/2007
(Continued)

OTHER PUBLICATIONS

Bayard et al. (Journal of Pharmacokinetics and Pharmacodynamics, 2004, 31(1), 75-107).*

(Continued)

*Primary Examiner* — Larry D Riggs, II
(74) *Attorney, Agent, or Firm* — Gilberto M. Villacorta; Jessica A. Flores; Foley & Lardner LLP

(57) ABSTRACT

Apparatus for monitoring a substance in human or animal in real time, the apparatus comprising a sensor providing a time series of measurements of substance level, said measurements being indicative of an inferred level of said substance in a part of said human or animal and a processor which applies an interacting multiple model strategy to a system model to provide a combined estimate of the inferred substance level from the substance level measurements. The substance may be glucose. The apparatus may also be adapted to control said substance using said interacting multiple model strategy to a system model to provide a combined estimate of a dose to be applied.

34 Claims, 3 Drawing Sheets

(51) Int. Cl.
  *G06G 7/48* (2006.01)
  *G06G 7/58* (2006.01)
  *G06F 19/00* (2011.01)

(56) References Cited

U.S. PATENT DOCUMENTS

| | | | |
|---|---|---|---|
| 5,086,229 | A | 2/1992 | Rosenthal et al. |
| 5,325,098 | A | 6/1994 | Blair et al. |
| 5,497,772 | A * | 3/1996 | Schulman et al. ............ 600/347 |
| 6,572,545 | B2 | 6/2003 | Knobbe et al. |
| 6,575,905 | B2 | 6/2003 | Knobbe et al. |
| 6,876,925 | B2 | 4/2005 | Syrjarinne |
| 7,079,991 | B2 | 7/2006 | Li et al. |
| 2003/0050546 | A1 | 3/2003 | Desai et al. |
| 2003/0208113 | A1 | 11/2003 | Mault et al. |

FOREIGN PATENT DOCUMENTS

| | | |
|---|---|---|
| JP | 2005-328924 | 12/2005 |
| JP | 2007-512588 | 5/2007 |
| WO | WO-97/28787 A1 | 8/1997 |
| WO | WO-02/24065 A1 | 3/2002 |
| WO | WO-2005/041103 | 5/2005 |
| WO | WO 2005/072792 A1 | 8/2005 |

OTHER PUBLICATIONS

Hovorka et al. (Physiol. Meas., 2004, 905-920).*
Abolmaesumi et al.; "An Interacting Multiple Model Probabilistic Data Association Filter for Cavity Boundary Extraction From Ultrasound Images"; IEEE Trans. Med. Imaging; 23 (6):772-784, 2004.
Australian Office Action dated Mar. 16, 2012 as received in corresponding Australian Application No. 2008309313, 2 pages.
Bayard, et al.; "A Bayesian Approach to Tracking Patients Having Changing Pharmacokinetic Parameters"; J. Pharamacokinet. Pharmacodyn.; 31 (1):75-107, 2004.
Hovorka, et al.; "Nonlinear Model Predictive Control of Glucose Concentration in Subjects With Type 1 Diabetes"; Physiol Meas.; 25 (4):905-920, 2004.
Hovorka; "Continuous Glucose Monitoring and Closed-Loop Systems"; Diabet. Med.; 23 (1): 1-12, 2006.
Knobbe, et al.; "The Extended Kalman Filter for Continuous Glucose Monitoring"; Diabetes Technol. Ther.; 7 (1):15-27, 2005.
Linkens, et al.; "Generalized Predictive Control With Feedforward (Gpcf) for Multivariable Anesthesia"; International Journal of Control; 56 (5):1039-1057, 1992.
Mahfouf, et al.; "Non-Linear Generalized Predictive Control (NLGPC) Applied to Muscle Relaxant Anaesthesia"; International Journal of Control; 71 (2):239-257, 1998.
Mazor, et al.; "Interacting Multiple Model In Target Tracking: A Survey"; IEEE Transactions on Aerospace and Electronic Systems; 34 (1):103-123, 1998.
Parker et al.; "A Model-Based Algorithm for Blood Glucose Control in Type 1 Diabetic Patients"; IEEE Trans. Biomed. Eng; 46 (2):148-157, 1999.
Parker et al.; "The Intravenous Route to Blood Glucose Control"; IEEE Eng. Med. Biol. Mag.; 20 (1):65-73, 2001.
Rebrin, et al.; "Subcutaneous Glucose Predicts Plasma Glucose Independent of Insulin: Implications for Continuous Monitoring"; American Journal of Physiology—Endocrinology and Metabolism; 277 (3):E561-E571, 1999.
Sartori, et al.; "On-Line Estimation of Propofol Pharmacodynamic Parameters"; Annual International Conference of the IEEE Engineering in Medicine and Biology Society; 1 74-7, 2005.
Steil, et al.; "Feasibility of Automating Insulin Delivery for the Treatment of Type 1 Diabetes"; Diabetes; 55 (12):3344-3350, 2006.
Struys, et al.; "Closed Loops in Anaesthesia"; Best. Pract. Res. Clin. Anaesthesiol.; 20 (1):211-220, 2006.
Official Action issued Aug. 8, 2013 in corresponding European Application No. 08806748.3.
Wilinska, M. et al., "Interstitial glucose kinetics in subjects with type 1 diabetes under physiologic conditions," Metabolism, vol. 53, No. 11, Nov. 1, 2004, pp. 1484-1491, XP004609590.

* cited by examiner

SUBSTANCE MONITORING AND CONTROL IN HUMAN OR ANIMAL BODIES

CROSS-REFERENCE TO RELATED APPLICATIONS

This application is a National Stage application of PCT/GB2008/050932, filed Oct. 10, 2008, which claims the priority of Great Britain Patent Application No. 0719969.8, filed Oct. 12, 2007. The foregoing applications are incorporated by reference herein in their entirety.

This application relates to monitoring and controlling levels of substances, e.g. glucose, in human or animal bodies.

BACKGROUND

Insulin is secreted by the pancreas in a highly controlled fashion to maintain the plasma glucose concentration within a narrow physiological range. In type 1 diabetes, insulin is administered exogenously to mimic the basal and postprandial insulin needs. The standard therapy is based on multiple insulin injections using a combination of short and long acting insulin analogues supported by blood glucose self-monitoring. Treatment by the continuous subcutaneous insulin infusion (CSII), i.e. using insulin pumps, is on the rise.

Continuous glucose monitoring promises to improve glucose control in subjects with diabetes (D. C. Klonoff. Continuous Glucose Monitoring: Roadmap for 21st century diabetes therapy. Diabetes Care 28 (5):1231-1239, 2005). New minimally invasive and non-invasive techniques are being developed; see examples such as U.S. Pat. No. 5,086,229 and U.S. Pat. No. 5,497,772.

Supporting the development of new minimally invasive and non-invasive measurement techniques, a range of mathematical methods has been proposed to aid data processing. Data processing is confounded by measurements of the glucose sensor being normally carried out in a fluid distinct from plasma, such as in the interstitial, dermal, or tear fluid. The kinetics properties of the transfer between plasma and the measurement fluid result in a delay between plasma and the measurement fluid (K. Rebrin, G. M. Steil, W. P. Van Antwerp, and J. J. Mastrototaro. Subcutaneous glucose predicts plasma glucose independent of insulin: implications for continuous monitoring. American Journal of Physiology-Endocrinology and Metabolism 277 (3):E561-E571, 1999). Thus, the ratio between the plasma glucose and the glucose in the measurement fluid changes with time and appropriate techniques are required to calculate an estimate of plasma glucose from sensor measurements apart from filtering out the measurement error.

The extended (linearised) Kalman filter has been proposed as a suitable computational vehicle for data processing of glucose sensor signal, see U.S. Pat. No. 6,575,905, U.S. Pat. No. 6,572,545, WO02/24065 and E. J. Knobbe and B. Buckingham. "The extended Kalman filter for continuous glucose monitoring" (Diabetes Technol. Ther. 7 (1):15-27, 2005). Process noise is an integral component of the Kalman filter. The process noise represents the random disturbance which is not captured by the other model components and is distinct from the measurement error, which describes the random component of the measurement process. The characteristics of the process noise are usually obtained from retrospective analysis of experimental data. However, the characteristics and specifically the variance of the process noise may be subject to temporal variations due to physiological or lifestyle factors excluded from modelling. For example, following meal ingestion, the process noise will have considerably higher variance compared to that applicable to fasting conditions. The standard Kalman filter is unable to accommodate and correct for such temporal variations because it uses fixed values for the process noise.

There are other known methods for monitoring glucose levels, for example WO97/28787 uses an adaptive mathematic model and U.S. Pat. No. 5,497,772 uses an enzymatic sensor to sense glucose levels.

The advancements in the field of continuous glucose sensors have stimulated the development of closed-loop systems based on combination of a continuous monitor, a control algorithm, and an insulin pump (R. Hovorka. Continuous glucose monitoring and closed-loop systems. Diabet. Med. 23 (1):1-12, 2006). This is denoted as an artificial pancreas. The original concept was introduced in late 70's, see U.S. Pat. No. 4,055,175 and U.S. Pat. No. 4,464,170, for example.

A wide spectrum of control algorithms has been proposed to titrate insulin in a closed-loop fashion, see a review by Parker et al (R. S. Parker, F. J. Doyle, III, and N. A. Peppas. The intravenous route to blood glucose control. IEEE Eng. Med. Biol. Mag. 20 (1):65-73, 2001). Two main categories have been employed, classical feedback control embodied in the proportional-integral-derivative (PID) controller (G. M. Steil, K. Rebrin, C. Darwin, F. Hariri, and M. F. Saad. Feasibility of automating insulin delivery for the treatment of type 1 diabetes. Diabetes 55 (12):3344-3350, 2006), and model predictive control (MPC) (R. Hovorka, V. Canonico, L. J. Chassin, U. Haueter, M. Massi-Benedetti, Federici M. Orsini, T. R. Pieber, H. C. Schaller, L. Schaupp, T. Vering, and M. E. Wilinska. Nonlinear model predictive control of glucose concentration in subjects with type 1 diabetes. Physiol Meas. 25 (4):905-920, 2004).

The Kalman filter was also used as part of control algorithm for closed-loop glucose control (R. S. Parker, F. J. Doyle, III, and N. A. Peppas. A model-based algorithm for blood glucose control in type I diabetic patients. IEEE Trans. Biomed. Eng 46 (2):148-157, 1999). A linearised Kalman filter was also proposed, see U.S. Pat. No. 6,572,545. The Kalman filter or the extended Kalman filter (described above) provide computationally efficient means to track and predict glucose excursions and are used in combination with a physiologically-based glucoregulatory model represented by stochastic differential equations.

There are other known methods for controlling glucose levels, for example, US2003/0208113 describes a system for assisting a person to maintain blood glucose levels between predetermined limits and U.S. Pat. No. 4,055,175 describes glucose control using a model based on quadratic and biquadratic equations.

Statements of Invention

According to the invention there is provided a method of real time substance monitoring in a living human or animal, the method comprising:
inputting a time series of substance level measurements from a sensor, said substance level measurements being indicative of a inferred level of said substance in a part of said human or animal,
calculating a first estimate of said inferred substance level from said measured substance level using a first system model,
calculating a second estimate of said inferred substance level from said measured substance level using a second system model with said second system model being a variation of said first system model and
predicting a combined estimate of the inferred substance level based on a combination of the first and second estimates.

By using multiple models, the method may be considered to use an interacting multiple model strategy, i.e. a strategy in which two or more models may be defined with each model being a variation of the system model. Thus, in other words, according to another aspect of the invention, there is provided a method of real time substance monitoring in a living human or animal, the method comprising: inputting a time series of substance level measurements from a sensor, said substance level measurements being indicative of a inferred level of said substance, defining a system model which estimates said inferred substance level from said measured substance level, and applying an interacting multiple model strategy to the system model to provide a combined estimate of the inferred substance level.

The combined estimate may be a combined estimate of the current inferred substance level or a combined estimate of a future inferred substance level.

Each variation of the model may have a different process noise. As explained previously, the process noise represents the random disturbance which is not captured by the other model components. For each model, an estimate of the inferred substance level and the process noise is calculated in a computationally efficient manner. The estimates for each model are combined to provide a combined estimate of the inferred substance level. When combining the estimates, each estimate is preferably weighted according to an associated mixing probability, i.e. a probability of the estimate representing the true value. In other words, if one model is the most likely, this model is given the highest weighting so that the combined estimate is based primarily on this model. If no one model is the most likely, the weightings may be adjusted accordingly to give a more balanced representation of each model in the overall estimate. Said mixing probability may be updated responsive to a difference between said predicted glucose level measurement of each respective said model and said glucose level measurement from said sensor.

As an alternative to defining the models to have different process noise, the multiple models defined by the interacting multiple model strategy may differ in certain model constants. As described in the prior art, the extended Kalman filter may be used for a model which is non-linear in a certain parameter. However, the extended Kalman filter approximates the solution and for highly non-linear models this may be a problem. Using the interacting multiple model strategy permits the definition of a number of models, each differing in the fixed level of the parameter causing non-linearity. These models run in parallel, with no approximations being necessary (albeit the models are confined to discrete levels of the non-linear parameter) and the most appropriate parameter level may be chosen.

The interacting multiple model (IMM) strategy has been introduced to allow computationally efficient tracking of a maneuvering target (E. Mazor, A. Averbuch, Y. Bar-Shalom, and J. Dayan. Interacting multiple model methods in target tracking: A survey. IEEE Transactions on Aerospace and Electronic Systems 34 (1):103-123, 1998). A maneuvering target is characterised by temporal variability in acceleration, where the acceleration is, in effect, the process noise.

Besides use in radar and GPS tracking, see for example U.S. Pat. No. 5,325,098, U.S. Pat. No. 7,079,991, and U.S. Pat. No. 6,876,925, in the biomedical field the IMM approach has been used to monitor kinetic parameters (D. S. Bayard and R. W. Jelliffe. A Bayesian approach to tracking patients having changing pharmacokinetic parameters. J. Pharmacokinet. Pharmacodyn. 31 (1):75-107, 2004) and the imaging field, see for example (P. Abolmaesumi and M. R. Sirouspour. An interacting multiple model probabilistic data association filter for cavity boundary extraction from ultrasound images. IEEE Trans. Med. Imaging 23 (6):772-784, 2004).

The present applicant has recognised that the IMM is well suited to handle the temporal variations of the process noise of substance monitoring, for example when using a Kalman filter described above.

The substance being monitored is preferably glucose and the model is a glucoregulatory model. For glucose monitoring, the inferred glucose level may be the plasma glucose concentration which is not directly measurable and the measured glucose level may be the interstitial glucose level. The glucose level may be measured intravenously, subcutaneously and/or intradermally.

The glucoregulatory model may comprise five sub-models, the sub-model of insulin absorption, the sub-model of insulin action, the sub-model of gut absorption, the sub-model of glucose kinetics, and the sub-model of interstitial glucose kinetics. Alternatively, the glucoregulatory model may consist of a sub-set of the five models, e.g. the sub-model of glucose kinetics and the sub-model of interstitial glucose kinetics which interact to predict the inferred glucose level, e.g. plasma glucose concentration, from the measured glucose level, e.g. glucose level in the interstitial fluid.

For glucose monitoring, the process noise may represent the change in the unexplained glucose influx. The interacting multiple model strategy may comprise defining for each variation of the model, a state vector comprising a set of variables each having an associated uncertainty. The set of variables may comprise variables representing glucose amounts in the accessible, non-accessible and/or interstitial compartments and a variable representing an unexplained change in glucose level.

Alternatively, the substance being monitored may be the depth of anaesthesia. More information on the control of anaesthesia and the appropriate models which may be used in the interacting multiple model strategy may be determined from EP 1278564 and related application EP 1725278 to Aspect Medical Systems Inc. Other references are D. A. Linkens and M. Mahfouf. "Generalized Predictive Control with Feedforward (Gpcf) for Multivariable Anaesthesia." *International Journal Of Control* 56 (5):1039-1057, 1992, M. Mahfouf and D. A. Linkens. "Non-linear generalized predictive control (NLGPC) applied to muscle relaxant anaesthesia." *International Journal Of Control* 71 (2):239-257, 1998, M. M. Struys, E. P. Mortier, and Smet T. De. "Closed loops in anaesthesia." *Best. Pract. Res. Clin. Anaesthesiol.* 20 (1):211-220, 2006 or V Sartori, P Schumacher, T Bouillon, M Luginbuehl and M Morari "On-line estimation of propofol pharmacodynamic parameters." *Annual International Conference of the IEEE Engineering in Medicine and Biology Society* (2005), 1 74-7.

The method may comprise applying a Kalman filter. A Kalman filter has two distinct steps; a predict step which uses the state estimate from the previous timestep to produce an estimate of the state at the current timestep and an update step which comprises using measurements at the current timestep to refine the estimate from the predict step to arrive at a new, more accurate, state estimate for the current timestep. In other words, the method may comprise predicting the state estimate from the previous timestep to produce an estimate of the state at the current timestep and updating the estimate using measurements at the current timestep to refine the estimate from the predicting step to arrive at an updated state estimate for the current timestep. The covariance, i.e. a measure of the estimated accuracy of the state estimate, may be used when refining the estimate. The update step may also comprise updating the covariance.

The method may further comprise predicting an estimate for the mixing probability and updating the predicted estimate for the mixing probability based on measurements of the substance levels. The combined estimate preferably uses the updated mixing probability estimates.

The method may further comprise an interact step which links the various models. The interact step may comprise determining the mixing probability from the mode probability, i.e. the probability that the system model transitions from one variation model to another variation model.

According to another aspect of the invention there is a method of real time glucose monitoring in a living human or animal, the method comprising
- inputting a time series of glucose level measurements from a glucose sensor;
- constructing at least two state vectors each comprising a set of variables for a respective one of at least two glucose level models, said state vectors representing states of said at least two models, said state vectors also including a variable representing an uncertainty in a change in glucose level with time, each of said variables having an associated probability distribution;
- predicting a value of a said glucose level using said probability distribution and said state vectors;
- updating values of said state vectors responsive to a difference between a predicted glucose level measurement for each said model and a glucose level measurement from said sensor; and
- determining a combined predicted glucose level measurement for said human or animal by combining outputs from said glucose level models according to a mixing probability representing a respective probability of each said model correctly predicting said glucose level; and
- further comprising updating said mixing probability responsive to said predicted glucose level measurement of each respective said model and said glucose level measurement from said sensor.

The method may further comprise using the value of a first of state vectors to modify a second of said state vectors to thereby represent a transition between said models.

According to another aspect there is provided a method of controlling a substance in a human or animal in real time, the method comprising
- obtaining a combined estimate for the inferred substance level as previously described,
- inputting a desired reference value for the inferred substance level
- calculating, using said combined estimate, a dose to obtain said desired reference value and
- applying said dose to a patient.

According to another aspect there is provided a method for real time control of a substance in a human or animal, the apparatus comprising:
- calculating a combined estimate using real time monitoring as described above, and
- calculating a specified amount of medication as the amount of medication required to bring the combined estimate into line with a desired value and
- delivering said specified amount of medication to a user.

Additionally or alternatively, the calculation of the specified amount and/or does may be calculated using a method similar to that used for monitoring and the combined estimate may be calculated by any other method.

Thus, according to another aspect there is provided a method for real time control of a substance in a human or animal, the method comprising providing a time series of measurements of substance level, said measurements being indicative of an inferred level of said substance in a part of said human or animal, calculating an estimate of said inferred level, calculating a specified amount of medication to be the amount of medication required to bring the estimate of said inferred level in line with a desired value by calculating a first estimate of said specified amount of medication using a first system model, calculate a second estimate of said specified amount of medication using a second system model with said second system model being a variation of said first system model, calculating said specified amount of medication based on a combination of said estimates and delivering said specified amount of medication to a user. The method may further comprise calculating said estimate of said inferred level using real time monitoring as described above.

The substance being controlled may be glucose and the dose/medication applied may be insulin, glucagons or similar substances or a combined thereof. The substance being controlled may be the depth of anaesthesia glucose and the dose/medication applied may be anaesthesia.

According to another aspect of the invention, there is provided a method for controlling glucose in human or animal body, comprising calculating a combined estimate using real time monitoring as described above, and displaying a suggested insulin bolus to be applied on a user interface, wherein the suggested insulin bolus is calculated by the processor as the amount of medication required to bring the combined estimate into line with a desired glucose value. The method may comprise using the interacting multiple model strategy described above to calculate the insulin bolus to be applied.

According to another aspect there is provided apparatus for monitoring a substance in human or animal in real time, the apparatus comprising:
- a sensor providing a time series of measurements of substance level, said measurements being indicative of an inferred level of said substance in a part of said human or animal and
- a processor which is adapted to perform the following steps:
  calculate a first estimate of said inferred substance level from said measured substance level using a first system model,
  calculate a second estimate of said inferred substance level from said measured substance level using a second system model with said second system model being a variation of said first system model and
predicting a combined estimate of the inferred substance level based on a combination of the first and second estimates.

By using multiple models, the method may be considered to use an interacting multiple model strategy, i.e. a strategy in which two or more models may be defined with each model being a variation of the system model. Thus, in other words, according to another aspect of the invention there is provided apparatus for monitoring a substance in human or animal in real time, the apparatus comprising:
- a sensor providing a time series of measurements of said substance level, said measurements being indicative of an inferred level of said substance in a part of said human or animal and
- a processor which applies an interacting multiple model strategy to a system model to provide a combined estimate of the inferred substance level from the substance level measurements.

The substance being monitored is preferably glucose and the model is a glucoregulatory model. For glucose monitoring, the inferred glucose level may be the plasma glucose concentration which is not directly measurable and the measured glucose level may be the interstitial glucose level. The glucose level may be measured intravenously, subcutaneously and/or intradermally.

Alternatively, the substance being monitored may be the depth of anaesthesia.

The processor may be a state estimator and the interacting multiple model strategy may comprise defining for each variation of the model, a state vector comprising a set of variables each having an associated uncertainty. The set of variables may comprise variables representing glucose amounts in the accessible, non-accessible and/or interstitial compartments and a variable representing an unexplained change in glucose level.

The glucoregulatory model may comprise five sub-models, the sub-model of insulin absorption, the sub-model of insulin action, the sub-model of gut absorption, the sub-model of glucose kinetics, and the sub-model of interstitial glucose kinetics. Alternatively, the glucoregulatory model may consist of a sub-set of the five models, e.g. the sub-model of glucose kinetics and the sub-model of interstitial glucose kinetics.

The apparatus may further comprise a user monitor with an input/output interface to receive inputs from the user, e.g. meals and exercise information and to display the status of the apparatus.

The apparatus may further comprise a real-time alarm which is activated when the combined estimate is below a preset hypoglycaemia threshold or above a preset hyperglycaemia threshold.

According to another aspect there is provided apparatus for monitoring glucose in human or animal in real time, the apparatus comprising:
 (an input or) a continuous glucose sensor providing an estimate of glucose level
 an optimal state estimator based on the interacting multiple model strategy and adopting a stochastic model to provide optimal estimate of glucose level from data obtained by the continuous glucose sensor The interacting multiple model strategy may use a standard or extended Kalman filter.

The apparatus may comprise one or more additional glucose sensors providing independent estimates of glucose level. At least one sensor may measure glucose intravenously. At least one sensor may measure glucose subcutaneously. At least one sensor may measure glucose subcutaneously. At least one sensor may measure glucose intradermally.

The apparatus may further comprise a user monitor with an input/output interface to receive inputs from the user and to display the status of the apparatus.

The apparatus may further comprise a real-time alarm which is activated when the optimal glucose estimate is below a preset hypoglycaemia threshold or above a preset hyperglycaemia threshold.

The apparatus may use the interacting multiple model strategy to make a prediction of future glucose values and/or to indicate sensor failure when the estimate of the process noise exceeds a predefined value.

According to another aspect of the invention, there is provided apparatus for real time control of glucose in a human or animal, the apparatus comprising:
 a glucose sensor providing a time series of measurements of glucose level, said measurements being indicative of plasma glucose concentration,
 a processor which applies an interacting multiple model strategy to a glucoregulatory model to provide a combined estimate of the plasma glucose concentration from the measured glucose levels, and
 a dispenser for delivering a specified amount of medication to a user in response to a command from the processor, wherein the specified amount of medication is calculated by the processor as the amount of medication required to bring the combined estimate into line with a desired glucose value.

The dispenser may deliver insulin or insulin and glucagon, or insulin and another glucose controlling substance.

According to another aspect of the invention, there is provided apparatus for controlling glucose in human or animal body, comprising
 a glucose sensor providing a time series of measurements of glucose level, said measurements being indicative of plasma glucose concentration,
 a processor which applies an interacting multiple model strategy to a glucoregulatory model to provide a combined estimate of the plasma glucose concentration from the measured glucose levels, and
 a user interface for displaying a suggested insulin bolus to be applied
 wherein the suggested insulin bolus is calculated by the processor as the amount of medication required to bring the combined estimate into line with a desired glucose value.

The desired glucose value may vary with time to define a trajectory of desired or set-point values. The trajectory may be input to the processor by a user, e.g. via a user interface which accepts input from a user.

The processor may comprise a model combiner to generate a combined estimate for the plasma glucose concentration using the interacting multiple model strategy and may comprise a dose estimator which applies the interacting multiple model strategy to determine the amount of medication required.

According to another aspect of the invention, there is provided an apparatus for controlling a substance in human or animal in real time, the apparatus comprising:
 an input to receive an estimate of the said substance
 an input to receive past control commands
 an input to receive the desired set point trajectory of the said substance
 an interacting multiple model strategy providing optimal estimate of the said substance
 an optimal dose estimator relating the control command to the time evolution of the said substance with the use of substantially the same interacting multiple model strategy
 a dispenser, which delivers the amount of medication specified by the control command.

The interacting multiple model strategy may use a standard or extended Kalman filter.

The substance being controlled is preferably glucose and the medication may be insulin or a combination of insulin and glucagons.

Alternatively, the substance being controlled may be the depth of anaesthesia and the medication may be anaesthesia.

The set point trajectory may be predefined, e.g. obtained from a health monitor which accepts input from a user.

According to another aspect of the invention, there is provided an artificial pancreas for controlling glucose levels in real time comprising:
 a continuous glucose monitor providing an estimate of glucose level
 an optimal state estimator based on the interacting multiple model strategy and adopting a stochastic physiological model of glucoregulation to provide optimal estimate of glucose level from data obtained by the continuous glucose monitor a glucose controller utilising a substantially same stochastic model of glucoregulation as the optimal glucose estimator and a substantially same interacting multiple model strategy to determine a control command a dispenser, which delivers the amount of medication specified by the control command The artificial pancreas may be a portable device. The dispenser may infuse insulin or a combination of insulin and glucagon. The dispenser may infuse medication intravenously or subcutaneously.

The artificial pancreas may comprise one or more additional glucose monitors providing independent estimates of glucose level. At least one monitor may measure glucose intravenously. At least one monitor may measure glucose subcutaneously.

The artificial pancreas may further comprise a user monitor with an input/output interface to receive inputs from the user and to display status of the artificial pancreas.

The interacting multiple model strategy may use a standard or extended Kalman filter.

The artificial pancreas may receive information about any or all of user triggered insulin boluses, meals, exercise and insulin infusion. This information may be utilised by the physiological model of glucoregulation.

According to another aspect of the invention there is provided a method for estimating retrospectively basal insulin infusion, carbohydrate-to-insulin ratio, and insulin sensitivity comprising the acts of:

receiving time-series of an estimate of glucose level receiving time-series of administered insulin infusion and insulin boluses providing the time-series to an interacting multiple model strategy, which adopts a stochastic physiological model of glucoregulation to provide optimal estimate basal insulin infusion, carbohydrate-to-insulin ratio, and insulin sensitivity According to another aspect of the invention there is provided a decision support system for suggesting in real time insulin bolus comprising:

a continuous glucose monitor providing an estimate of glucose level an optimal state estimator based on the interacting multiple model strategy and adopting a stochastic physiological model of glucoregulation to provide optimal estimate of glucose level from data obtained by the continuous glucose monitor a glucose controller utilising a substantially same stochastic model of glucoregulation as the optimal glucose estimator and a substantially same interacting multiple model strategy to determine insulin bolus a user monitor with an input/output interface to receive inputs from the user and to display the suggested insulin bolus a dispenser, which delivers the amount of medication specified by the control command The decision support system may further comprise a dispenser, which based on confirmation by the user delivers the insulin bolus. The insulin bolus may be a prandial insulin bolus or a correction insulin bolus.

The invention further provides processor control code to implement the above-described methods, in particular on a data carrier such as a disk, CD- or DVD-ROM, programmed memory such as read-only memory (Firmware), or on a data carrier such as an optical or electrical signal carrier. Code (and/or data) to implement embodiments of the invention may comprise source, object or executable code in a conventional programming language (interpreted or compiled) such as C, or assembly code, code for setting up or controlling an ASIC (Application Specific Integrated Circuit) or FPGA (Field Programmable Gate Array), or code for a hardware description language such as Verilog (Trade Mark) or VHDL (Very high speed integrated circuit Hardware Description Language). As the skilled person will appreciate such code and/or data may be distributed between a plurality of coupled components in communication with one another.

FIGURES

Figure 1A:
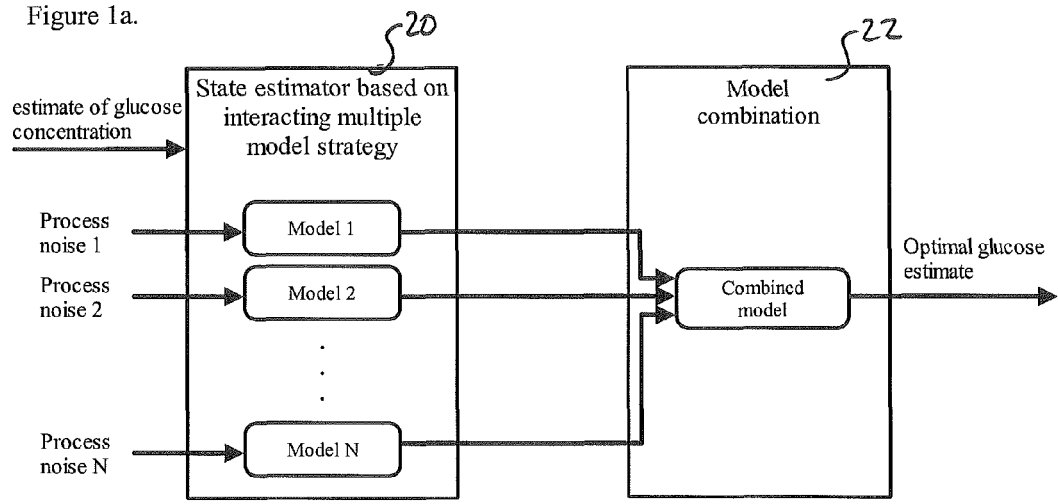
FIG. 1a is a schematic drawing showing how the interacting multiple model strategy is used to estimate glucose level.
Figure 3:
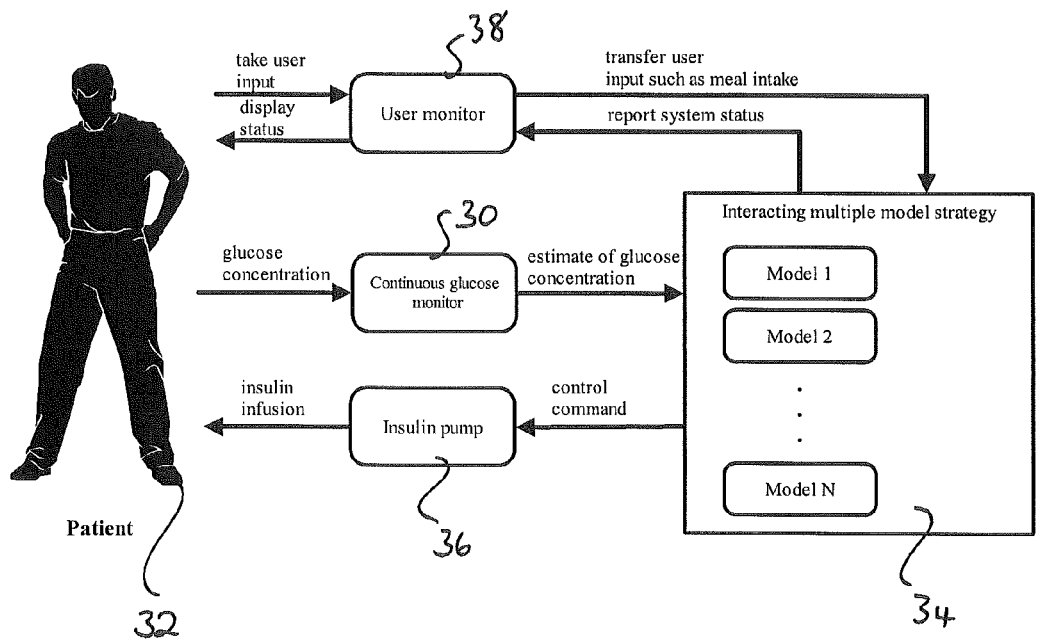

FIG. 3 is a schematic drawing of an artificial pancreas for controlling glucose levels in a patient using the interacting multiple model strategy FIG. 1a shows the key steps in using a multiple model strategy which is used to improve model tracking. The model used is a glucoregulatory model. Overall, N models are defined in a state estimator 20, with each model being a variation of the glucoregulatory model having a different process noise. As explained previously, the process noise represents the random disturbance which is not captured by the other model components and is distinct from the measurement error, which describes the random component of the measurement process. The characteristics of the process noise are usually obtained from retrospective analysis of experimental data. However, the characteristics and specifically the variance of the process noise may be subject to temporal variations. For each model an estimate of the state vector based on glucose measurements and the process noise is calculated in a computationally efficient manner. As an alternative to defining the models to have different process noise, the multiple models defined by the interacting multiple model strategy may differ in certain model constants.

The glucoregulatory may comprise five sub-models, the sub-model of insulin absorption, the sub-model of insulin action, the sub-model of gut absorption, the sub-model of glucose kinetics, and the sub-model of interstitial glucose kinetics. Alternatively, the glucoregulatory model may consist of a sub-set of the models described, e.g. the sub-model of glucose kinetics and the sub-model of interstitial glucose kinetics.

The insulin absorption sub-model is described by a two compartment (two depot) model $$\frac{di_1(t)}{dt} = -\frac{1}{t_{xI}}i_1(t) + \frac{u(t)}{60} + \delta_{t_j}(t)v(t) \quad (1)$$

$$\frac{di_2(t)}{dt} = -\frac{1}{t_{xI}}[i_2(t) - i_1(t)] \quad (2)$$

$$i(t) = \frac{1}{t_{xI}}\frac{1000}{MCR_I W}i_2(t) \quad (3)$$

where $i_1(t)$ and $i_2(t)$ is the amount of insulin in the two subcutaneous insulin depots (U), i(t) is the plasma insulin concentration (mU/l), u(t) denotes insulin infusion (U/h), v(t) denotes insulin boluses given at time $t_j$(U), $t_{max,I}$ is the time-to-peak of insulin absorption (min), $MCR_I$ is the metabolic clearance rate of insulin (L/kg/min), and W is subject's weight (kg).

The insulin action sub-model is described as $$\frac{dr_D(t)}{dt} = p_{2D}(i(t) - r_D(t)) \quad (4)$$

$$\frac{dr_E(t)}{dt} = p_{2E}(i(t) - r_E(t)) \quad (5)$$

where $\gamma_D$ and $\gamma_{EGP}$ are the remote insulin actions affecting glucose disposal and endogenous glucose production, respectively, (mU/l), and $p_{2,D}$ and $p_{2,EGP}$ are the fractional disappearance rates associated with the remote insulin actions (/min).

The gut absorption sub-model is described by a two compartment model $$\frac{da_1(t)}{dt} = -\frac{1}{t_{xG}}a_1(t) + v_G(t) \quad (6)$$

$$\frac{da_2(t)}{dt} = -\frac{1}{t_{xG}}[a_2(t) - a_1(t)] \quad (7)$$

$$u_A(t) = \frac{5.551}{Wt_{xG}}a_2(t) \quad (8)$$

where $a_1(t)$ and $a_2(t)$ is the amount of glucose in the two absorption compartments (g), $u_A(t)$ is the gut absorption rate (mmol/kg/min), $v_G(t)$ denotes meal ingestion (g/min), and $t_{max,G}$ is the time-to-peak of the gut absorption (min).

The glucose kinetics sub-model is described as $$\frac{dq_1(t)}{dt} = \quad (9)$$
$$-(S_{ID}x_D(t) + k_{21})q_1(t) + k_{12}q_2 - F_{01} + EGP(t) + Fu_A(t) + u_S(t)$$

$$\frac{dq_2(t)}{dt} = +k_{21}q_1(t) - k_{12}q_2(t) \quad (10)$$

$$g_P(t) = \frac{q_1(t)}{V_G} \quad (11)$$

where $q_1(t)$ and $q_2(t)$ are the masses of glucose in the accessible and non-accessible glucose compartments (mmol/kg), $k_{21}$ and $k_{12}$ are the fractional transfer rates (/min), $F_{01}$ is the non-insulin dependent glucose utilisation (mmol/kg/min), EGP(t) is the endogenous glucose production (mmol/kg/min), $S_{I,D}$ is peripheral insulin sensitivity (/min per mU/l), F is glucose bioavailability (unitless), $u_s(t)$ is unexplained glucose influx (mmol/kg/min), $g_P(t)$ is plasma glucose concentration, $V_G$ is the glucose distribution volume in the accessible compartment (l/kg).

The EGP is obtained as $$EGP(t) = EGP_B \exp\left(-(r_E(t) - BIC)\frac{\ln(2)}{I_{1/2}}\right) \quad (12)$$

where $EGP_B$ is the basal endogenous glucose production (mmol/kg/min), BIC is (basal) plasma insulin concentration resulting in plasma glucose concentration of 5.5 mmol/l (mU/l), and $I_{1/2}$ is an increment in the plasma insulin concentration halving the EGP (mU/l).

The change in unexplained glucose influx $u_s(t)$ (the process noise) is described by a stochastic differential equation $$du_s(t) = dw(t) \quad (13)$$

where w(t) is 1-dimensional driving Wiener process.

The basal insulin concentration BIC is calculated from the basal insulin requirement (BIR; U/h) as $$BIC = \frac{1000}{60} \frac{BIR}{MCR_I W} \quad (14)$$

where $MCR_I$ is the metabolic clearance rate of insulin (l/kg/min) and W is subject's weight (kg).

The interstitial glucose kinetics sub-model is described as $$\frac{dq_3(t)}{dt} = -k_{31}(q_3(t) - q_1(t)) \quad (15)$$

$$g_{IG}(t) = \frac{q_3(t)}{V_G} \quad (16)$$

where $q_3(t)$ is the mass of glucose in the interstitial fluid (mmol/kg), $k_{3I}$ is the fractional transfer rate (/min), and $g_{IG}(t)$ is interstitial glucose concentration.

As shown in FIG. 1a, a time series of glucose level measurements are inputted from a glucose sensor to the state estimator 20. These measurements may themselves be regarded as estimates for the plasma glucose concentration since they measure interstitial glucose levels. The state estimator 20 applies each model to calculate an estimate for the plasma glucose concentration. These estimates are combined in a modal combiner 22 to generate an optimal glucose estimate.

Figure 1B:
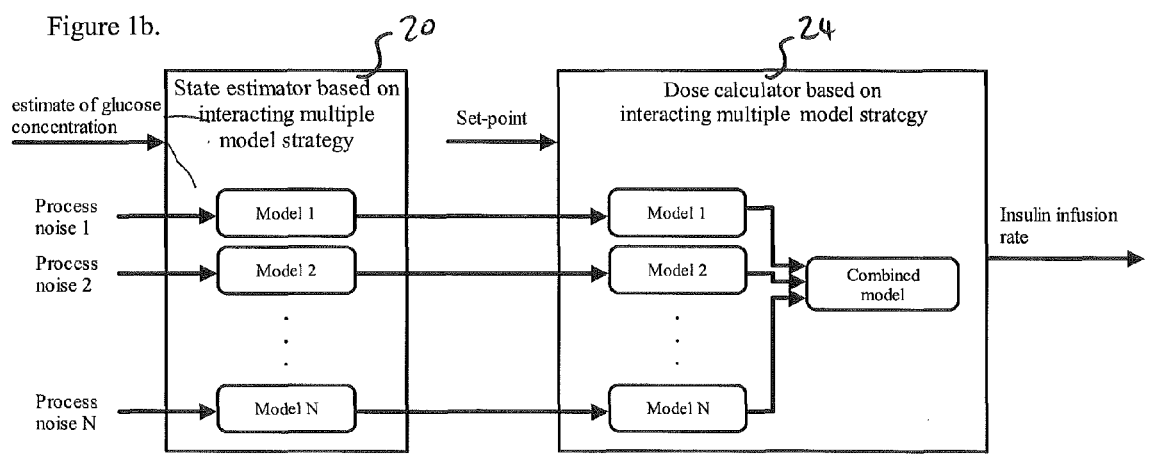
FIG. 1b is a schematic drawing which shows how the interacting multiple model strategy is used to estimate glucose level and to determine a dose based on this estimated level.
Figure 2:
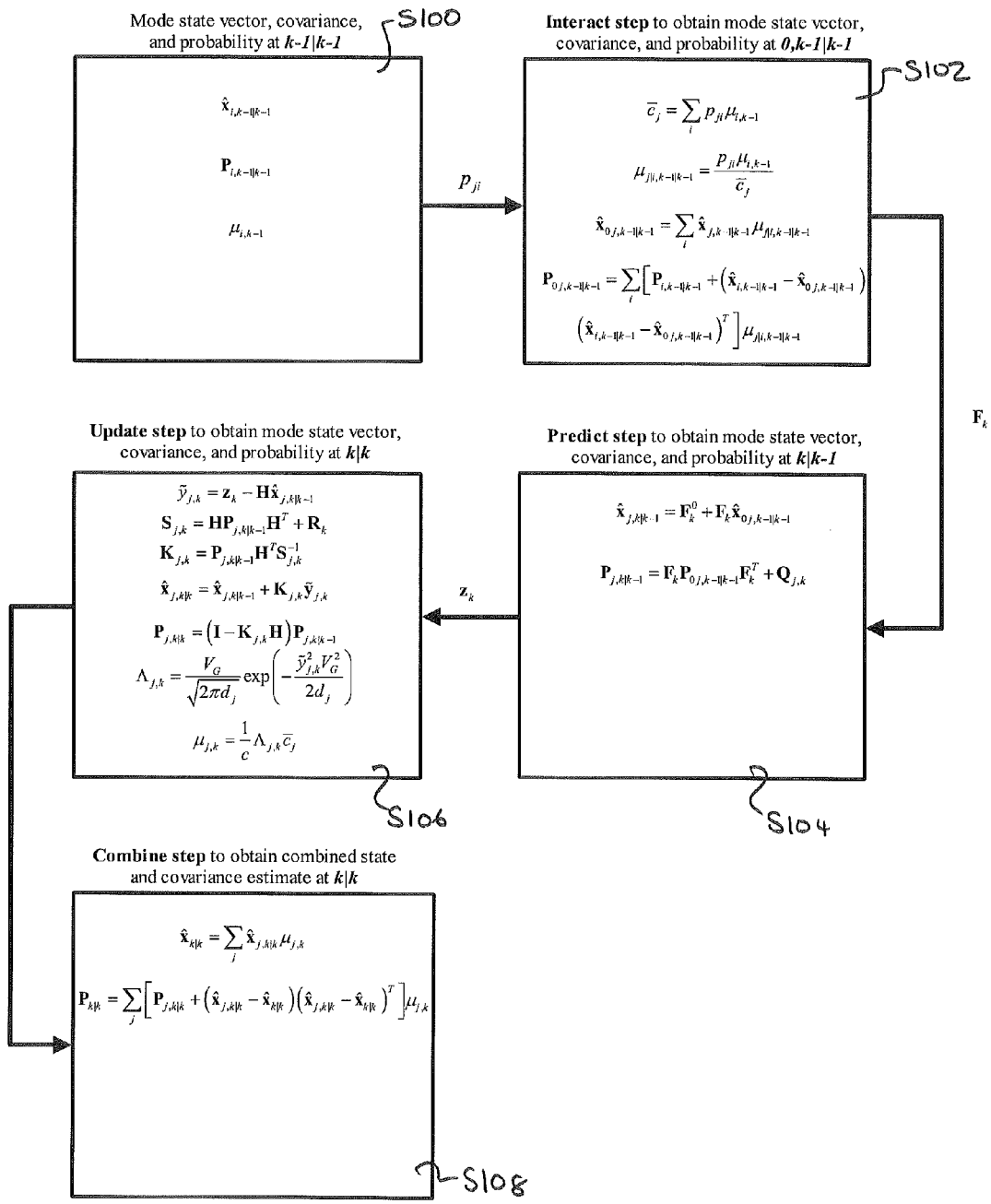
FIG. 2 is a flowchart showing the steps involved in the use of interacting multiple model strategy for state and covariance estimation.

FIG. 1b shows a variation of the system of FIG. 1a in which the model combiner is replaced by a dose calculator 24. The estimates from the state estimator are inputted to and combined in the dose calculator 24 to generate the optimal glucose estimate. A set-point representing the desired level of plasma glucose is also inputted to the dose calculator. The dose calculator 24 inputs the optimal glucose estimate into a control law to determine the dose to the applied so that a patient has the set-point level of plasma glucose. The calculated dose is the output insulin infusion rate More details of the strategy are shown in FIG. 2. The first step S100 is to define at time k−1, for each model i, a mode state vector $x_{i,k-1|k-1}$, a covariance $P_{i,k-1|k-1}$ and a mixing probability $\mu_{i,k-1|k-1}$. The covariance is a measure of the estimated accuracy of the state estimate. The mixing probability is the probability of each mode state vector being the true state vector and is the weighting attached to each state vector estimate when calculating the final state estimate.

The extended state vector $x_k$ which uses all the sub-models defined above includes nine states $$x_k^e = (i_{1,k}, i_{2,k}, r_{D,k}, r_{E,k}, a_{1,k}, a_{2,k}, q_{1,k}, q_{2,k}, q_{3,k}, u_{S,k})^T \quad (17)$$

where $i_{1,k}$ and $i_{2,k}$ is the amount of insulin in the two subcutaneous insulin depots at time k, $\gamma_{D,k}$ and $\gamma_{E,k}$ are the remote insulin actions affecting glucose disposal and endogenous glucose production, $a_{1,k}$ and $a_{2,k}$ are the amount of glucose in the two absorption compartments, $q_{1,k}$, $q_{2,k}$, $q_{3,k}$ represent glucose amounts in the accessible, non-accessible, and interstitial compartments and $u_{s,k}$ is the unexplained glucose influx (process noise).

The function $f$ is used to calculate the predicted state $x_k$ from the previous estimate $x_{k-1}$ $$x_k = f(x_{k-1}, u_k, w_k) \tag{18}$$

where $w_k$ is a 1-dimensional driving Wiener process (see 13)

$$z_k = h(x_k, v_k) \tag{19}$$

$z_k$ is the measurement at time k of the true state $x_k$
h is the observation model which maps the true state space into the observed space and
$v_k$ is the observation noise which is assumed to be zero mean Gaussian white noise with covariance $R_k$ (see also eqn 60 below)

The state transition for $i_{1,k}$ (i.e. the transition from time k−1 to time k) is defined by the following expressions $$i_{1,k} = f_{10} + f_{11} i_{1,k-1} \tag{20}$$

where $$f_{10} = \frac{u_k t_{xI,k-1}}{60}\left(1 - e^{-\frac{\Delta t_k}{t_{xI,k-1}}}\right) \tag{21}$$

$$f_{11} = e^{-\frac{\Delta t_k}{t_{xI,k-1}}} \tag{22}$$

The state transition for $i_{2,k}$ is defined by the following expressions $$i_{2,k} = f_{20} + f_{21} i_{1,k-1} + f_{22} i_{2,k-1} \tag{23}$$

where $$f_{20} = f_{10} - f_{11}\frac{u_k \Delta t_k}{60} \tag{24}$$

$$f_{21} = f_{11}\frac{\Delta t}{t_{xI,k-1}} \tag{25}$$

$$f_{22} = f_{11} \tag{26}$$

The state transition for $r_{D,k}$ is defined by the following expressions $$r_{D,k} = f_{30} + f_{31} i_{1,k-1} + f_{32} i_{2,k-1} + f_{33} r_{D,k-1} \tag{27}$$

$$f_{30} = \begin{cases} \frac{50 u_k}{3 MCR_I W}\left[1 - \frac{f_{33} + p_{2D} f_{11}(p_{2D} t_{xI,k-1}(\Delta t_k + t_{xI,k-1}) - \Delta t_k - 2t_{xI,k-1})}{(p_{2D} t_{xI,k-1} - 1)^2}\right] & \text{if } p_{2D} \neq \frac{1}{t_{xI,k-1}} \\ \frac{50 u_k}{3 MCR_I W}\left[1 - f_{11}\frac{t_{xI,k-1}^2 + (\Delta t + t_{xI,k-1})^2}{2 t_{xI,k-1}^2}\right] & \text{otherwise} \end{cases} \tag{28}$$

$$f_{31} = \begin{cases} \frac{1000 p_{2,D}}{MCR_I W(p_{2D} t_{xI,k-1} - 1)^2}\left(f_{33} + f_{11}\frac{p_{2D} t_{xI,k-1} \Delta t_k - \Delta t_k - t_{xI,k-1}}{t_{xI,k-1}}\right) & \text{if } p_{2D} \neq \frac{1}{t_{xI,k-1}} \\ \frac{500 \Delta t_k^2 f_{11}}{MCR_I W t_{xI,k-1}^3} & \text{otherwise} \end{cases} \tag{29}$$

$$f_{32} = \begin{cases} \frac{1000 p_{2D}}{MCR_I W(p_{2D} t_{xI,k-1} - 1)}(f_{11} - f_{33}) & \text{if } p_{2D} \neq \frac{1}{t_{xI,k-1}} \\ \frac{1000 \Delta t_k f_{11}}{MCR_I W t_{xI,k-1}^2} & \text{otherwise} \end{cases} \tag{30}$$

$$f_{33} = e^{-p_{2D} \Delta t_k} \tag{31}$$

The state transition for $r_{E,k}$ is defined by the following expressions $$r_{E,k} = f_{40} + f_{41} i_{1,k-1} + f_{42} i_{2,k-1} + f_{44} r_{E,k-1} \tag{32}$$

$$f_{40} = \begin{cases} \frac{50 u_k}{3 MCR_I W}\left[1 - \frac{f_{44} + p_{2E,k-1} f_{11}(p_{2E,k-1} t_{xI,k-1}(\Delta t_k + t_{xI,k-1}) - \Delta t_k - 2t_{xI,k-1})}{(p_{2E,k-1} t_{xI,k-1} - 1)^2}\right] \\ \quad \text{if } p_{2E,k-1} \neq \frac{1}{t_{xI,k-1}} \\ \frac{50 u_k}{3 MCR_I W}\left[1 - f_{11}\frac{t_{xI,k-1}^2 + (\Delta t + t_{xI,k-1})^2}{2 t_{xI,k-1}^2}\right] \text{ otherwise} \end{cases} \tag{33}$$

-continued $$f_{41} = \begin{cases} \dfrac{1000 p_{2E,k-1}}{MCR_I W(p_{2E,k-1}t_{xI,k-1}-1)^2}\left(f_{44}+f_{11}\dfrac{p_{2E,k-1}t_{xI,k-1}\Delta t_k - \Delta t_k - t_{xI,k-1}}{t_{max,I}}\right) \\ \text{if } p_{2E,k-1} \neq \dfrac{1}{t_{xI,k-1}} \\ \dfrac{500\Delta t_k^2 f_{11}}{MCR_I W t_{xI,k-1}^3} \text{ otherwise} \end{cases} \quad (34)$$

$$f_{42} = \begin{cases} \dfrac{1000 p_{2E,k-1}}{MCR_I W(p_{2E,k-1}t_{xI,k-1}-1)}\left(e^{-\frac{\Delta t_k}{t_{xI,k-1}}} - e^{-p_{2E,k-1}\Delta t_k}\right) \\ \text{if } p_{2E,k-1} \neq \dfrac{1}{t_{xI,k-1}} \\ \dfrac{1000\Delta t_k e^{-\frac{\Delta t_k}{t_{xI,k-1}}}}{MCR_I W t_{xI,k-1}^2} \text{ otherwise} \end{cases} \quad (35)$$

$$f_{44} = e^{-p_{2E,k-1}\Delta t_k} \quad (36)$$

The state transition for $a_{1,k}$ is defined by the following expressions $$a_{1,k} = f_{55} a_{1,k-1} \quad (37)$$

where $$f_{55} = e^{-\frac{\Delta t_k}{t_{xG,k-1}}} \quad (38)$$

The state transition for $a_{2,k}$ is defined by the following expressions $$a_{2,k} = f_{65} a_{1,k-1} + f_{66} a_{2,k-1} \quad (39)$$

where $$f_{65} = f_{55} \frac{\Delta t}{t_{xG,k-1}} \quad (40)$$

$$f_{66} = f_{55} \quad (41)$$

The state transitions for $q_{1,k}$, $q_{2,k}$, and $q_{3,k}$ are defined by the following expressions $$q_{1,k} = f_{7,0} + f_{77} q_{1,k-1} + f_{78} q_{2,k-1} + f_{79} u_{S,k-1} \quad (42)$$

$$q_{2,k} = f_{8,0} + f_{87} q_{1,k-1} + f_{88} q_{2,k-1} + f_{89} u_{S,k-1} \quad (43)$$

$$q_{3,k} = f_{12,0} + f_{12,7} q_{1,k-1} + f_{12,8} q_{2,k-1} + f_{12,12} q_{3,k-1} + f_{12,9} u_{S,k-1} \quad (44)$$

where coefficients $f_{70}$, $f_{77}$, $f_{78}$, $f_{79}$, $f_{80}$, $f_{87}$, $f_{88}$, $f_{89}$, $f_{12,0}$, $f_{12,7}$, $f_{12,8}$, $f_{12,9}$, and $f_{12,12}$ can be obtained algebraically as described in Appendix or by numerical approximations.

The state transitions for $u_{S,K}$ is an identity, i.e.

$$u_{S,k} = u_{S,k-1} \quad (45)$$

Considering a subset state vector $x_k$, which includes states with associated uncertainty $$x_k = (q_{1f,k}, q_{2f,k}, u_{S,k}, F_k, q_{3f,k})^T \quad (46)$$

where $q_{1f,k}$, $q_{2f,k}$, and $q_{3f,k}$ represent glucose amounts in the accessible, non-accessible, and interstitial compartments excluding the contribution from meals (more correctly the last meal), $u_{s,k}$ is (as before) the unexplained glucose influx (process noise) and $F_k$ is the state transition model which is applied to the previous state $x_{k-1}$ (see eqn 55).

The total amount of glucose in the compartments is calculated as $$q_{1,k} = q_{1f,k} + q_{1m,k} \quad (47)$$

$$q_{2,k} = q_{2f,k} + q_{2m,k} \quad (48)$$

$$q_{3,k} = q_{3f,k} + q_{3m,k} \quad (49)$$

where $q_{1m,k}$, $q_{2m,k}$, and $q_{3m,k}$ represent glucose amounts in the accessible, non-accessible, and interstitial compartments due to the (last) meal.

The glucose masses due to the meal are calculated as $$q_{1m,k} = F_k f_{7,10} \quad (50)$$

$$q_{2m,k} = F_k f_{8,10} \quad (51)$$

$$q_{3m,k} = F_k f_{12,10} \quad (52)$$

The state transition is obtained as $$x_k = F_k^0 + F_k x_{k-1} + G_k w_k \quad (53)$$

where $F_k^0$ is the additive transition model which is independent of the previous state $x_{k-1}$ and the process noise $$F_k^0 = \begin{bmatrix} f_{70} \\ f_{80} \\ 0 \\ 0 \\ f_{12,0} \end{bmatrix} \quad (54)$$

and $F_k$ is the state transition model which is applied to the previous state $x_{k-1}$ $$F_k = \begin{bmatrix} f_{77} & f_{78} & f_{79} & 0 & 0 \\ f_{87} & f_{88} & f_{89} & 0 & 0 \\ 0 & 0 & f_{11,11} & 0 & 0 \\ 0 & 0 & 0 & 1 & 0 \\ f_{12,7} & f_{12,8} & f_{12,9} & 0 & f_{12,12} \end{bmatrix} \quad (55)$$

and $G_k$ is the additive transition model which is applied to the process noise $w_k$ $$G_k = \begin{bmatrix} g_1 \Delta t_k \\ g_2 \Delta t_k \\ \Delta t_k \\ 0 \\ g_5 \Delta t_k \end{bmatrix} \quad (56)$$

and the change in the unexplained glucose influx (process noise) $w_k$ is normally distributed, with zero mean and standard deviation $\sigma_{w,k} = \sigma_w / \sqrt{\Delta t_k}$.

If a glucose measurement is not made in time instance $t_k$, the unexplained glucose influx is regressed towards zero with a half-time $m_{1/2}$ $$f_{11,11} = \exp\left(-\Delta t_k \frac{\ln(2)}{m_{1/2}}\right) \quad (57)$$

otherwise $$f_{11,11} = 1 \quad (58)$$

We find that the covariance $Q_k$ of the unexplained glucose influx is $$Q_k = \text{cov}(G_k w_k) = \sigma_{w,k}^2 G_k G_k^T \quad (59)$$

At each time interval, a measurement $z_k$ of interstitial glucose concentration is made. This measurement is noisy measurement of the plasma glucose. The measurement noise is normally distributed with mean 0 and standard deviation $\sigma_{Z,k}$ $$z_k = H x_k + v_k \quad (60)$$

where

H is the observation model which maps the true state space into the observed space $$H = [0 \ 0 \ 0 \ f_{12,10}/V_G \ 1/V_G] \quad (61)$$

and $v_k$ is the observation noise which is assumed to be zero mean Gaussian white noise with covariance $R_k$ $$R_k = E[v_k v_k^T] = [\sigma_{Z,k}^2] \quad (62)$$

The initial starting position is assumed identical to the first glucose measurement $\tilde{g}_{IG,0}$ and an apriori bioavailability $\tilde{F}$ $$\hat{x}_{0|0} = \begin{bmatrix} \tilde{g}_{IG,0} V_G \\ \tilde{g}_{IG,0} V_G \frac{k_{21}}{k_{12}} \\ 0 \\ F \\ \tilde{g}_{IG,0} V_G \end{bmatrix} \quad (63)$$

The uncertainty in glucose concentration and bioavailability is expressed in the initial value of the covariance matrix $P_{0|0}$ $$P_{0|0} = \begin{bmatrix} \sigma_{Z,0}^2 V_G^2 & 0 & 0 & 0 & 0 \\ 0 & \sigma_{Z,0}^2 V_G^2 \frac{k_{21}^2}{k_{12}^2} & 0 & 0 & 0 \\ 0 & 0 & 4EGP_B^2 & 0 & 0 \\ 0 & 0 & 0 & \sigma_F^2 & 0 \\ 0 & 0 & 0 & 0 & \sigma_{Z,0}^2 V_G^2 \end{bmatrix} \quad (64)$$

where $\sigma_F^2$ is the variance of the apriori distribution of bioavailability F.

A multiple model strategy is used to improve model tracking. Overall, N models are defined, which differ in the standard deviation of the unexplained glucose influx $w_k$ $$\sigma_{w1,k} = \sigma_{w1}/\sqrt{\Delta t_k}$$

$$\sigma_{w2,k} = \sigma_{w2}/\sqrt{\Delta t_k}$$

$$\ldots$$

$$\sigma_{wN,k} = \sigma_{wN}/\sqrt{\Delta t_k} \quad (65)$$

where $\sigma_{w(i-1)} < \sigma_{wi}$ without loss of generality.

The Markov transition probability from mode (or model) i to j is defined as $p_{ji}$, i.e. the probability that the system will switch from model i to model j is $p_{ji}$.

At step S102, there is an optional interact step to obtain for model 0, a mode state vector x, a covariance P and a mixing probability $\mu$ at time k−1. For i and j, the mixing probability $\mu_{j|i,k|k}$ at time k (the weights with which the estimates from the previous cycle k−1 are given to each filter at the beginning of the current cycle k) is defined as $$\mu_{j|i,k-1|k-1} = \frac{p_{ji} \mu_{i,k-1}}{\bar{c}_j} \quad (66)$$

where $\mu_{i,k}$ is the mode probability, i.e. probability of each model i being the true model, at time k, and $\bar{c}_j$ is a normalisation factor $$\bar{c}_j = \sum_i p_{ji} \mu_{i,k-1} \quad (67)$$

The model interaction for mode j proceeds as $$\hat{x}_{0j,k-1|k-1} = \sum_i \hat{x}_{j,k-1|k-1} \mu_{j|i,k-1|k-1} \quad (68)$$

$$P_{0j,k-1|k-1} = \quad (69)$$
$$\sum_i [P_{i,k-1|k-1} + (\hat{x}_{i,k-1|k-1} - \hat{x}_{0j,k-1|k-1})(\hat{x}_{i,k-1|k-1} - \hat{x}_{0j,k-1|k-1})^T]$$
$$\mu_{j|i,k-1|k-1}$$

At step S104, there is a predict step to obtain for each model j, an estimate for the mode state vector x, covariance P and mixing probability $\mu$ at time k based on the observations, up to and including time k−1. In other words, the predict step uses the state estimate from the previous timestep to produce an estimate of the state at the current timestep.

The predict step for mode j consists of $$\hat{x}_{j,k|k-1} = F_k^0 + F_k \hat{x}_{0j,k-1|k-1} \quad (70)$$

$$P_{j,k|k-1} = F_k P_{0j,k-1|k-1} F_k^T + Q_{j,k} \quad (71)$$

At step S106, there is an update step which uses measurement information at the current timestep k to refine for each model j, the estimates for the mode state vector x, covariance P and mixing probability μ for the current timestep obtained from step S104. The resulting estimates should be more accurate estimates for the current timestep.

In case of a glucose measurement $\tilde{g}_{IG,k}$, for each mode j the update consists of evaluating the measurement residual $\tilde{y}_{j,k}$ $$\tilde{y}_{j,k} = z_k - H\hat{x}_{j,k|k-1} = \left[\tilde{g}_{IG,k} - \frac{q_{j,3f,k|k-1} + F_{j,k|k-1}f_{12,10}}{V_G}\right] \quad (72)$$

then evaluating the residual covariance $S_{j,k}$ $$S_{j,k} = HP_{j,k|k-1}H^T + R_k \\ = \left[\frac{p_{j,k|k-1,55} + f_{12,10}p_{j,k|k-1,45} + f_{12,10}(p_{j,k|k-1,54} + f_{12,10}p_{j,k|k-1,44})}{V_G^2} + \sigma_{Z,k}^2\right] \quad (73)$$

The optimal Kalman gain is obtained as $$K_{j,k} = P_{j,k|k-1}H^T S_{j,k}^{-1} \quad (74)$$

$$= P_{j,k|k-1}\frac{V_G}{d_j}\begin{bmatrix}0\\0\\0\\f_{12,10}\\1\end{bmatrix}$$

$$= \frac{V_G}{d_j}\begin{bmatrix}p_{j,k|k-1,15} + f_{12,10}p_{j,k|k-1,14}\\p_{j,k|k-1,25} + f_{12,10}p_{j,k|k-1,24}\\p_{j,k|k-1,35} + f_{12,10}p_{j,k|k-1,34}\\p_{j,k|k-1,45} + f_{12,10}p_{j,k|k-1,44}\\p_{j,k|k-1,55} + f_{12,10}p_{j,k|k-1,54}\end{bmatrix}$$

where $$d_j = p_{j,k|k-1,55} + f_{12,10}p_{j,k|k-1,45} + f_{12,10}(p_{j,k|k-1,54} + f_{12,10}p_{j,k|k-1,44}) + \sigma_{Z,k}^2 V_G^2 \quad (75)$$

The updated state estimate is obtained as $$\hat{x}_{j,k|k} = \hat{x}_{j,k|k-1} + K_{j,k}\tilde{y}_{j,k} \quad (76)$$

$$= \hat{x}_{j,k|k-1} + \frac{\tilde{g}_{IG,k}V_G - q_{j,3f,k|k-1} - F_{j,k|k-1}f_{12,10}}{d_j}\begin{bmatrix}p_{j,k|k-1,15} + f_{12,10}p_{j,k|k-1,14}\\p_{j,k|k-1,25} + f_{12,10}p_{j,k|k-1,24}\\p_{j,k|k-1,35} + f_{12,10}p_{j,k|k-1,34}\\p_{j,k|k-1,45} + f_{12,10}p_{j,k|k-1,44}\\p_{j,k|k-1,55} + f_{12,10}p_{j,k|k-1,54}\end{bmatrix}$$

The updated estimate covariance for the optimal Kalman gain is obtained as $$P_{j,k|k} = (I - K_{j,k}H)P_{j,k|k-1} = \quad (77)$$

$$\begin{bmatrix}1 & 0 & 0 & -f_{12,10}\frac{k_{12,10}p_{j,k|k-1,14}}{d_j} & \frac{p_{j,k|k-1,15} +}{d_j} - \frac{f_{12,10}p_{j,k|k-1,14}}{d_j}\\0 & 1 & 0 & -f_{12,10}\frac{k_{12,10}p_{j,k|k-1,24}}{d_j} & \frac{p_{j,k|k-1,25} +}{d_j} - \frac{f_{12,10}p_{j,k|k-1,24}}{d_j}\\0 & 0 & 1 & -f_{12,10}\frac{k_{12,10}p_{j,k|k-1,34}}{d_j} & \frac{p_{j,k|k-1,35} +}{d_j} - \frac{f_{12,10}p_{j,k|k-1,34}}{d_j}\\0 & 0 & 0 & 1-f_{12,10}\frac{k_{12,10}p_{j,k|k-1,44}}{d_j} & \frac{p_{j,k|k-1,45} +}{d_j} - \frac{f_{12,10}p_{j,k|k-1,44}}{d_j}\\0 & 0 & 0 & -f_{12,10}\frac{k_{12,10}p_{j,k|k-1,54}}{d_j} & 1-\frac{f_{12,10}p_{j,k|k-1,54}}{d_j}\end{bmatrix} P_{j,k|k-1}$$

Alternatively, if $K_{j,k}$ is not the optimal Kalman gain, the updated estimate covariance is obtained as $$P_{j,k|k} = (I - K_{j,k}H)P_{j,k|k-1}(I - K_{j,k}H)^T + K_{j,k}R_k K_{j,k}^T \quad (78)$$

The likelihood function $\Lambda_{j,k}$ of mode j is obtained as $$\Lambda_{j,k} = \frac{V_G}{\sqrt{2\pi d_j}}\exp\left(-\frac{\tilde{y}_{j,k}^2 V_G^2}{2d_j}\right) \quad (79)$$

and the mode probability as $$\mu_{j,k} = \frac{1}{c}\Lambda_{j,k}\bar{c}_j \quad (80)$$

Finally at step S108, there is a combine step whereby the estimated states and covariances for each model are combined to prove overall state and covariance estimates. The overall estimated state vector is obtained from a summation of all estimated state vectors multiplied by their weighting or mixing probability. Similarly, the estimated covariance is derived from a summation of all estimated covariances taking into account the relevant mixing probabilities.

$$\hat{x}_{k|k} = \sum_j \hat{x}_{j,k|k} \mu_{j,k} \quad (81)$$

$$P_{k-1|k-1} = \sum_j [P_{j,k|k} + (\hat{x}_{j,k|k} - \hat{x}_{k|k})(\hat{x}_{j,k|k} - \hat{x}_{k|k})^T] \mu_{j,k} \quad (82)$$

Referring to FIG. 1b, the control law used by the dose calculator to determine the correct dose is defined as $$J = \sum_{j=N_1}^{N_2} [\hat{y}_{t+j|t} - w_{t+j}]^2 + \lambda \sum_{j=1}^{N_2-d} [\Delta \mu_{t+j-1}]^2 \quad (83)$$

where $\hat{y}_{t+j|t}$ is plasma glucose concentration obtained using the combined step defined by Eq. (81) and interstitial glucose measurements taken up to time t, and $$\Delta u_j = u_j - u_{j-1} \quad (84)$$

The extended input vector $u^+$ is defined as $$u^+ = (v_i, u)^T \quad (85)$$

where $v_i$ denotes insulin bolus given at time i and u is insulin infusion with the first element of u, $u_1$, defining the insulin infusion rate to be delivered.

Thus the control law in matrix notation is $$J = J_1 + J_2 = \|A(u^+ - u_r^+) + y_r - w\| + \|\Lambda(u - u^{-1})\| \quad (86)$$

where w is the set point (i.e. desired glucose level), $u_r$ is the operating point, $y_r$ is the output associated with the operating point, and A represents the model given by Eqs. (1)-(11) linearised around the operating point $$a_{ij} = \frac{1}{V_G} \frac{dq_{1,j}}{du_i^+} \quad (87)$$

with the matrix $\Lambda$ defined as $$\Lambda = \begin{pmatrix} \lambda_{t+1} & 0 & \cdots & \cdots & 0 \\ 0 & \lambda_{t+2} & & & \vdots \\ \vdots & & \ddots & & \vdots \\ \vdots & & & \lambda_{t+N-1} & 0 \\ 0 & \cdots & \cdots & 0 & \lambda_{t+N} \end{pmatrix} \quad (88)$$

The two components of the control law $J_1$ and $J_2$ and their partial derivatives with respect to $u^+$ can be written as $$J_1 = u^{+T} A^T A u^+ 2[(y_r - w)^T - u_r^{+T} A^T]Au + [u_r^{+T} A^T - 2(y_r - w)^T] A u_r^+ - 2w^T y_r + y_r^T y_r + w^T w \quad (89)$$

$$J_2 = (u - u^{-1})^T \Lambda^T \Lambda (u - u^{-1}) \quad (90)$$

$$\frac{dJ_1}{du^+} = 2A^T Au^+ + 2A^T(y_r - w - Au_r^+) \quad (91)$$

$$\frac{dJ_2}{du^+} = 2(B^T B u^+ + b) \text{ with} \quad (92)$$

$$B = \begin{pmatrix} 0 & 0 & \cdots & \cdots & \cdots & 0 \\ 0 & -\lambda_{t+1} & 0 & & & \vdots \\ 0 & \lambda_{t+2} & -\lambda_{t+2} & 0 & & \vdots \\ \vdots & 0 & & \ddots & & 0 \\ 0 & & & \lambda_{t+N-1} & -\lambda_{t+N-1} & 0 \\ 0 & \cdots & \cdots & 0 & \lambda_{t+N} & -\lambda_{t+N} \end{pmatrix} \quad (93)$$

$$B^T B = \begin{pmatrix} 0 & 0 & 0 & \cdots & \cdots & 0 \\ 0 & \lambda_{t+1}^2 + \lambda_{t+2}^2 & -\lambda_{t+2}^2 & 0 & & \vdots \\ 0 & -\lambda_{t+2}^2 & \lambda_{t+2}^2 + \lambda_{t+3}^2 & -\lambda_{t+3}^2 & & \vdots \\ \vdots & 0 & & \ddots & & 0 \\ 0 & & & -\lambda_{t+N-2}^2 & \lambda_{t+N-2}^2 + \lambda_{t+N-1}^2 & -\lambda_{t+N}^2 \\ 0 & \cdots & & 0 & -\lambda_{t+N-1}^2 & \lambda_{t+N-1}^2 + \lambda_{t+N}^2 \end{pmatrix} \quad (94)$$

and $$b = (0 \quad -\lambda_{t+1}^2 u_t \quad 0 \quad \cdots \quad 0)^T \quad (95)$$

The derivative of J with respect to $u^+$ is then obtained as $$\frac{dJ}{du^+} = 2(Cu^+ + c) = 0 \quad (96)$$

where $$C = A^T A + B^T B \quad (97)$$

$$c = A^T(y_r - w - Au_r^+) + b \quad (98)$$

The solution is found as $$u^+ = -C^{-1} c \quad (99)$$

FIG. 3 is a schematic showing apparatus implementing the method of controlling levels of glucose described above. The apparatus comprises at least one continuous glucose monitor 30 which measures the glucose concentration in a patient 32 at regular time intervals which may be every minute, every hour or another user defined interval. The glucose monitor may measure glucose levels intravenously, subcutaneously and/or intradermally. The measured glucose levels provide an initial estimate of the patient's inferred glucose level, e.g. plasma glucose concentration.

The measured glucose levels are input to a processor 34 which calculates a refined estimate of glucose level using the interacting multiple model strategy. The processor 34 uses the refined estimated to calculate a dose to be applied to the patient. The processor 34 is connected to an insulin pump 36 and delivers a control command to the insulin pump 36 in apply the calculated insulin infusion rate to the patient.

The apparatus also comprises an optional user monitor 38 which is connected to the processor 34. The user monitor 38 has an input interface to receive inputs from the user such as meal intake, exercise, etc. This information is input to the processor 34 to use when calculating the refined glucose estimate and dose. The user monitor 38 also receives system status information from the processor and has an output interface to display such information to the patient.

No doubt many effective alternatives will occur to the skilled person. It will be understood that the invention is not limited to the described embodiments and encompasses modifications apparent to those skilled in the art lying within the spirit and scope of the claims appended hereto.

APPENDIX

This appendix describes the closed-form approximation of coefficients $f_{70}$, $f_{77}$, $f_{78}$, $f_{79}$, $f_{80}$, $f_{87}$, $f_{88}$, $f_{89}$, $f_{12,0}$, $f_{12,7}$, $f_{12,8}$, $f_{12,9}$, and $f_{12,12}$.

The first element of u, $u_1$, defines the insulin infusion rate to be delivered. The amount of glucose appearing during the time interval $[t_{k-1}, t_k)$ can be approximated by a linear function $u_G(t)$ (mmol/kg/min) as $$u_G(t) = u_{G,k-1} + \frac{u_{G,k} - u_{G,k-1}}{\Delta t_k} t + u_{S,k-1} \qquad (100)$$

where $$u_{G,k} = \begin{cases} EGP_k - F_{01,k} + u_{A,k} & \text{if bioavailability is not estimated} \\ EGP_k - F_{01,k} & \text{if bioavailability is estimated} \end{cases} \qquad (101)$$

The fractional first order turnover rate $k_{01}$ from the accessible glucose compartment is obtained as a piecewise constant approximation during the time interval $\Delta t_k$ $$k_{01}(t) = k_{01,k} = S_{ID} \frac{x_D(t_{k-1}) + x_D(t_k)}{2} \qquad (102)$$

Denote $r_k$ the rate of change in $u_k$ $$r_k = \frac{u_{G,k} - u_{G,k-1}}{\Delta t_k} \qquad (103)$$

Define the auxiliary variables $v_1$ to $v_{18}$ $$v_1 = k_{01} + k_{12} \qquad (104)$$
$$v_2 = (k_{01} - k_{12})^2 + k_{21}(2v_1 + k_{21})$$
$$v_3 = v_1 + k_{21}$$
$$v_4 = k_{01} k_{12}$$
$$v_5 = \sqrt{v_2}$$
$$v_6 = k_{12} - k_{31}$$
$$v_7 = k_{12} + k_{21}$$
$$v_8 = k_{12}(k_{12} + (k_{21} - k_{31})) + k_{21} k_{31} - k_{01} v_6$$
$$v_9 = 2v_2(v_4 - k_{31}(v_3 - k_{31}))$$
$$v_{10} = v_4(k_{21} - v_6) - k_{01} k_{21}(k_{31} - 2k_{21})$$
$$v_{11} = \frac{1}{v_5}(k_{01} - k_{12} + k_{21})$$
$$v_{12} = e^{-k_{31}\Delta t_k}$$
$$v_{13} = e^{-\frac{1}{2}\Delta t_k (v_3 + v_5)}$$
$$v_{14} = e^{\Delta t_k v_5}$$
$$v_{15} = v_{13}(v_{14} - 1)$$
$$v_{16} = v_{13}(v_{14} + 1)$$
$$v_{17} = v_2(v_6 + k_{21})$$
$$v_{18} = v_5(k_{01}(k_{21} - v_6) + v_7(v_6 + k_{21}))$$

Then $$f_{77} = \frac{(v_{16} - v_{15} v_{11})}{2} \qquad (105)$$

$$f_{87} = \frac{k_{21} v_{15}}{v_5} \qquad (106)$$

$$f_{12,7} = \frac{k_{31}}{v_9}(v_{13}(-v_6 v_2 + v_5 v_8 - v_{14}(v_6 v_2 + v_5 v_8)) + 2v_2 v_6 v_{12}) \qquad (107)$$

$$f_{78} = \frac{v_{15} k_{12}}{v_5} \qquad (108)$$

$$f_{88} = \frac{(v_{16} + v_{15} v_{11})}{2} \qquad (109)$$

$$f_{12,8} = \qquad (110)$$
$$\frac{k_{31} k_{12}}{v_9}(v_{13}(-v_2 + v_5(v_3 - 2k_{31})) - v_{14}(v_2 + v_5(v_3 - 2k_{31}))) + 2v_2 v_{12})$$

$$f_{79} = \frac{1}{k_{01}}\left[1 + \frac{v_{13}}{2v_5}(v_7 - k_{01} - v_5 + (k_{01} - v_5 - v_7)v_{14})\right] \qquad (111)$$

$$f_{89} = \frac{k_{21}}{v_4}\left[1 + \frac{v_{13}}{2}\left(\frac{v_3}{v_5} - 1 - \left(\frac{v_3}{v_5} + 1\right)v_{14}\right)\right] \qquad (112)$$

$$f_{12,9} = \frac{1}{k_{01}}\left[1 + \frac{1}{v_9}(k_{31} v_{13}(v_{17} - v_{18} + (v_{17} + v_{18})v_{14}) - 2v_2 v_6 v_{12} k_{01})\right] \qquad (113)$$

The partial derivatives $g_1 = \partial q_{1,k}/\partial u_{G,k}$, $g_2 = \partial q_{2,k}/\partial u_{G,k}$, and $g_5 = \partial q_{3,k}/\partial u_{G,k}$ can be obtained as $$g_1 = \frac{1}{\Delta t_k k_{01}}\left[\Delta t_k - \frac{1}{v_4}\left(v_7 - \frac{v_{13}}{2v_5}(v_7(v_5 - v_7) + k_{01}(k_{12} - k_{21}) + (v_7(v_7 + v_5) + k_{01}(k_{21} - k_{12}))v_{14})\right)\right] \qquad (114)$$

$$g_2 = \frac{k_{21}}{\Delta t_k v_4}\left[\Delta t_k - \frac{1}{v_4}\left(v_3 - \frac{v_{13}}{2v_5}((v_5(2v_3 - v_7 - k_{01}) + 2v_4 - v_3^2) + (v_3(v_3 + v_5) - 2v_4)v_{14})\right)\right] \qquad (115)$$

-continued $$g_5 = \frac{1}{(v_6(k_0 - k_{31}) - k_{21}k_{31})\Delta t_k} \left[ \frac{v_9}{2v_2 k_{01}} \left( \Delta t_k - \frac{v_7 k_{31} + v_4}{v_4 k_{31}} \right) + \right.$$
$$\left( \frac{k_{31} v_{13}}{2v_4 v_5 k_{01}} (k_{01} k_{21}(k_{01} - v_5) + +(v_7 - v_5)v_7(v_6 + k_{21}) + \right.$$
$$v_{10} - v_{14}(k_{01} k_{21}(v_5 + k_{01}) +$$
$$\left. \left. (v_5 + v_7)v_7(v_6 + k_{21}) + v_{10}) + \frac{v_{12} v_6}{k_{31}} \right) \right]$$
(116)

These partial derivatives can be used to calculate other coefficients $$f_{70} = f_{79} u_{G,k-1} + g_1 r_k \quad (117)$$

$$f_{80} = f_{89} u_{G,k-1} + g_2 r_k \quad (118)$$

$$f_{12,0} = f_{12,9} u_{G,k-1} + g_5 r_k \quad (119)$$

$$f_{12,12} = v_{12} \quad (120)$$

The coefficients $k_{7,10,k}$, $k_{8,10,k}$, and $k_{12,10,k}$ at time $t_k$ are calculated recursively using corresponding coefficients $k_{7,10,k-1}$, $k_{8,10,k-1}$, and $k_{12,10,k-1}$ obtained in the previous time instance $t_{k-1}$ $$f_{7,10} = f_{7,10,k-1} f_{77} + f_{8,10,k-1} f_{78} + f_{79} u_{A,k-1} + g_1(u_{A,k} - u_{A,k-1}) \quad (121)$$

$$f_{8,10} = f_{8,10,k-1} f_{88} + f_{7,10,k-1} f_{87} + f_{89} u_{A,k-1} + g_2(u_{A,k} - u_{A,k-1}) \quad (122)$$

$$f_{12,10} = f_{12,10,k-1} f_{12,12} + f_{7,10,k-1} f_{12,7} + f_{8,10,k-1} f_{12,8} + f_{12,9} u_{A,k-1} + g_5(u_{A,k} - u_{A,k-1}) \quad (123)$$

The invention claimed is:

1. Apparatus for real time control of glucose in a human or an animal, the apparatus comprising:
   a sensor providing a time series of measurements of glucose level, said measurements being indicative of an inferred level of said glucose in a part of said human or animal,
   a processor which is adapted to perform the following steps:
      calculate a first estimate of said inferred glucose level from said measured glucose level using a first glucoregulatory system model,
      calculate a second estimate of said inferred glucose level from said measured glucose level using a second glucoregulatory system model with said second system model being a variation of said first system model, and
      predict a combined estimate of the inferred glucose level based on a combination of the first and second estimates,
   wherein the processor is a state estimator and is adapted to define a state vector for each model, the state vector comprising a set of variables each having an associated uncertainty, the set of variables including a variable representing an unexplained change in glucose level with each model having a different standard deviation in the unexplained change in glucose level;
   wherein the first and second glucoregulatory models each comprise a sub-model of glucose kinetics in the blood of said human or animal, a sub-model of interstitial glucose kinetics, a sub-model of insulin absorption, a sub-model of insulin action and a sub-model of gut absorption; and
   wherein the state vector includes the following states $$x_k = (q_{1f,k} q_{2f,k} u_{S,k} F_k q_{3f,k})^T$$

where $q_{1f,k}$, $q_{2f,k}$, and $q_{3f,k}$ represent glucose amounts in the accessible, non-accessible, and interstitial compartments excluding the contribution from meals, $u_{s,k}$ is the unexplained glucose influx and $F_k$ is glucose availability, and a dispenser that delivers a specified amount of medication to a user in response to a command from the processor based on the predicted combined estimate of the inferred glucose level.

2. Apparatus according to claim 1, wherein the processor is adapted to calculate a combined estimate by weighting each estimate according to an associated mixing probability representing a respective probability of each said model correctly predicting said glucose level.

3. Apparatus according to claim 2, wherein the processor is further adapted to update said mixing probability responsive to a difference between said predicted glucose level measurement of each respective said model and said glucose level measurement from said sensor.

4. Apparatus according to claim 1, further comprising a user monitor to receive inputs from the user and/or to display the status of the apparatus.

5. Apparatus according to claim 1, wherein the sensor measures the glucose intravenously, subcutaneously and/or intradermally.

6. Apparatus according to claim 1, further comprising a real-time alarm which is activated when the combined estimate or the combined estimate of future glucose level is below a preset hypoglycaemia threshold or above a preset hyperglycaemia threshold.

7. Apparatus for real time control of a substance in a human or an animal, the apparatus comprising:
   a sensor providing a time series of measurements of substance level, said measurements being indicative of an interred level of said substance in a part of said human or animal,
   a processor which applies an interacting multiple model strategy to a system model to predict a combined estimate of the inferred substance level from the substance level measurements,
   wherein the interacting multiple model strategy comprises first and second glucoregulatory models each of which comprise a sub-model of glucose kinetics in the blood of said human or animal, a sub-model of interstitial glucose kinetics, a sub-model of insulin absorption, a sub-model of insulin action and a sub-model of gut absorption;
   wherein said inferred substance level comprises a level of glucose in said blood and said substance level measurements comprise measurements of an interstitial glucose level;
   wherein the processor is a state estimator and is adapted to define a state vector for each model, the state vector comprising a set of variables each having an associated uncertainty, the set of variables including a variable representing an unexplained change in glucose level with each model having a different standard deviation in the unexplained change in glucose level;
   wherein the state vector includes the following states $$x_k^e = (i_{1,k} i_{2,k} r_{D,k} r_{E,k} a_{1,k} a_{2,k} q_{1,k} q_{3,k} u_{S,k})^T$$

where $i_{1,k}$ and $i_{2,k}$ is the amount of insulin in the two subcutaneous insulin depots at time k, $r_{D,k}$ and $r_{E,k}$ are the remote insulin actions affecting glucose disposal and endogenous glucose production, $a_{1,k}$ and $a_{2,k}$ are the amount of glucose in the two absorption compartments $q_{1,k}$, $q_{2,k}$, $q_{3,k}$ represent glucose amounts in the accessible, non-accessible, and interstitial compartments and $u_{s,k}$ is the unexplained glucose influx; and wherein said processor is configured to apply the interacting multiple model strategy to calculate a first estimate for said inferred glucose level from said measured substance level using said first glucoregulatory system model, calculate a second estimate for said inferred glucose level from said measured substance level using said second glucoregulatory system model and predict said combined estimate of the inferred glucose level based on a combination of said first and second estimates, and a dispenser that delivers a specified amount of medication to a user in response to a command from the processor based on the predicted combined estimate of the inferred glucose level.

8. Apparatus for real time control of glucose in a human or an animal, the apparatus comprising:
a sensor providing a time series of measurements of glucose level, said measurements being indicative of an inferred level of said glucose in a part of said human or animal;
a processor which is adapted to
construct at least two state vectors each comprising a set of variables for a respective one of at least two glucose level models, said state vectors representing states of said at least two models, said state vectors also including a variable representing an uncertainty in a change in glucose level with time, each of said variables having an associated probability distribution;
predict a value of a said glucose level using said probability distribution and said state vectors;
update values of said state vectors responsive to a difference between a predicted glucose level measurement for each said model and a glucose level measurement from said sensor;
update a mixing probability representing a respective probability of each said model correctly predicting said glucose level responsive to a difference between said predicted glucose level measurement of each respective said model and said glucose level measurement from said sensor; and
determine a combined predicted glucose level measurement for said human or animal by combining outputs from said glucose level models according to said updated mixing probability,
wherein said at least two models each comprise a sub-model of glucose kinetics in the blood of said human or animal, a sub-model of interstitial glucose kinetics, a sub-model of insulin absorption, a sub-model of insulin action and a sub-model of gut absorption; and
wherein the state vector includes the following states $$x_k = (q_{1f,k}, q_{2f,k}, u_{S,k}, F_k, q_{3f,k})^T$$

where $q_{1f,k}$, $q_{2f,k}$, and $q_{3f,k}$ represent glucose amounts in the accessible, non-accessible, and interstitial compartments excluding the contribution from meals, $u_{s,k}$ is the unexplained glucose influx and $F_k$ is glucose availability, and a dispenser that delivers a specified amount of medication to a user in response to a command from the processor based on the predicted combined estimate of the inferred glucose level.

9. Apparatus according to claim 1 or claim 7,
wherein the processor is adapted to calculate the specified amount of medication as the amount of medication required to bring the combined predicted glucose level measurement into line with a desired value.

10. Apparatus for real time control of a substance in a human or an animal, the apparatus comprising
a sensor providing a time series of measurements of substance level, said measurements being indicative of an inferred level of said substance in a part of said human or animal,
a processor which is adapted to calculate an estimate of said inferred level, and
a dispenser that delivers a specified amount of medication to a user in response to a command from the processor based on the calculated estimate of said inferred level,
wherein the processor is adapted to calculate the specified amount of medication as the amount of medication required to bring the estimate of said inferred level in line with a desired value by
calculating a first estimate of said specified amount of medication using a first system model,
calculating a second estimate of said specified amount of medication using a second system model with said second system model being a variation of said first system model, and
calculating a combined estimate of said specified amount of medication based on a combination of the first and second estimates,
wherein said first system model and said second system model each comprise a sub-model of glucose kinetics in the blood of said human or animal, a sub-model of interstitial glucose kinetics, a sub-model of insulin absorption, a sub-model of insulin action and a sub-model of gut absorption;
wherein said inferred substance level comprises a level of said glucose in said blood and said substance level measurements comprises measurements of an interstitial glucose level;
wherein the processor is a state estimator and is adapted to define a state vector for each model, the state vector comprising a set of variables each having an associated uncertainty, the set of variables including a variable representing an unexplained change in glucose level with each model having a different standard deviation in the unexplained change in glucose level; and
wherein the state vector includes the following states $$x_k = (q_{1f,k}, q_{2f,k}, u_{S,k}, F_k, q_{3f,k})^T$$

where $q_{1f,k}$, $q_{2f,k}$, and $q_{3f,k}$ represent glucose amounts in the accessible, non-accessible, and interstitial compartments excluding the contribution from meals, $u_{s,k}$ is the unexplained glucose influx and $F_k$ is glucose availability.

11. Apparatus according to claim 10, wherein the dispenser delivers insulin, glucagon or a similar medication or combinations thereof.

12. Apparatus according to claim 1 or claim 7, comprising a user interface for displaying a suggested insulin bolus to be applied,
wherein the suggested insulin bolus is calculated by the processor as the amount of medication required to bring the combined estimate into line with a desired glucose value.

13. Apparatus according to claim 10, wherein the desired glucose value varies with time to define a trajectory of values.

14. Apparatus according to claim 12, wherein the processor applies an interacting multiple model strategy to the first and second glucoregulatory models to determine the amount of medication required.

15. A computer-implemented method for real time control of glucose in a living human or an animal, the method comprising:
inputting, to a processor, a time series of glucose level measurements from a sensor, said glucose level measurements being indicative of a inferred level of said glucose in a part of said human or animal, calculating, using said processor, a first estimate of said inferred glucose level from said measured substance level using a first glucoregulatory system model, calculating, using said processor, a second estimate of said inferred glucose level from said measured substance level using a second glucoregulatory system model with said second system model being a variation of said first system model, defining, using said processor, a state vector for each model, the state vector comprising a set of variables each having an associated uncertainty, the set of variables including a variable representing an unexplained change in substance level with each model having a different standard deviation in the unexplained change in substance level;

wherein the first and second glucoregulatory models each comprise a sub-model of glucose kinetics in the blood of said human or animal, a sub-model of interstitial glucose kinetics, a sub-model of insulin absorption, a sub-model of insulin action and a sub-model of gut absorption;

wherein said inferred substance level comprises a level of said glucose in said blood and said substance level measurements comprises measurements of an interstitial glucose level;

wherein the state vector includes the following states $$x_k = (q_{1f,k}, q_{2f,k}, u_{S,k}, F_k, q_{3f,k})^T$$

where $q_{1f,k}$, $q_{2f,k}$, and $q_{3f,k}$ represent glucose amounts in the accessible, non-accessible and interstitial events excluding the contribution from meals, $u_{s,k}$ is the unexplained glucose influx and $F_k$ is glucose availability, predicting, using said processor, a combined estimate of the inferred glucose level based on a combination of the first and second estimates, and delivering a specified amount of medication to a user in response to a command from the processor based on the predicted combined estimate of the inferred glucose level.

16. A method according to claim 15, comprising applying, using said processor, a Kalman filter.

17. A method according to claim 16, wherein each estimate is weighted, using said processor, according to a mixing probability representing a respective probability of each said model correctly predicting said glucose level when combining the multiple estimates.

18. A method according to claim 17, comprising updating, using said processor, said mixing probability responsive to a difference between said predicted glucose level measurement of each respective said model and said glucose level measurement from said sensor.

19. A method according to claim 17, comprising determining, using said processor, the mixing probability from the model probability.

20. A method according to claim 15, comprising measuring the glucose level intravenously, subcutaneously and/or intradermally.

21. A computer-implemented method for real time control of glucose in a living human or an animal, the method comprising inputting a time series of glucose level measurements from a glucose sensor;

constructing, using said processor, at least two state vectors each comprising a set of variables for a respective one of at least two glucose level models, said state vectors representing states of said at least two models, said state vectors also including a variable representing an uncertainty in a change in glucose level with time, each of said variables having an associated probability distribution;

predicting, using said processor, a value of a said glucose level using said probability distribution and said state vectors;

updating, using said processor, values of said state vectors responsive to a difference between a predicted glucose level measurement for each said model and a glucose level measurement from said sensor;

updating, using said processor, a mixing probability representing a respective probability of each said model correctly predicting said glucose level responsive to a difference between said predicted glucose level measurement of each respective said model and said glucose level measurement from said sensor; and determining, using said processor, a combined predicted glucose level measurement for said human or animal by combining outputs from said glucose level models according to said updated mixing probability, wherein said at least two models each comprise a sub-model of glucose kinetics in the blood of said human or animal, a sub-model of interstitial glucose kinetics, a sub-model of insulin absorption, a sub-model of insulin action and a sub-model of gut absorption, and wherein the state vector includes the following states $$x_k^e = (i_{1,k}, i_{2,k}, r_{D,k}, r_{E,k}, a_{1,k}, a_{2,k}, q_{1,k}, q_{2,k}, q_{3,k}, u_{S,k})^T$$

where $i_{1,k}$ and $i_{2,k}$ is the amount of insulin in the two subcutaneous insulin depots at time k, $r_{D,k}$ and $r_{E,k}$ are the remote insulin actions affecting glucose disposal and endogenous glucose production, $a_{1,k}$ and $a_{2,k}$ are the amount of glucose in the two absorption compartments, $q_{1,k}$, $q_{2,k}$, $q_{3,k}$ represent glucose amounts in the accessible, non-accessible, and interstitial compartments and $u_{s,k}$ is the unexplained glucose influx, and delivering a specified amount of medication to a user in response to a command from the processor based on the predicted combined estimate of the inferred glucose level.

22. A method according to claim 21, further comprising using the value of a first of state vectors to modify a second of said state vectors to thereby represent a transition between said models.

23. A method for real time control of a substance in a human or animal, the method comprising providing a time series of measurements of substance level to a processor, said measurements being indicative of an inferred level of said substance in a part of said human or animal, calculating, using said processor, an estimate of said inferred level, calculating, using said processor, a specified amount of medication to be the amount of medication required to bring the estimate of said inferred level in line with a desired value by calculating, using said processor, a first estimate of said specified amount of medication using a first system model, calculate, using said processor, a second estimate of said specified amount of medication using a second system model with said second system model being a variation of said first system model, calculating, using said processor, said specified amount of medication based on a combination of said estimates, and delivering said specified amount of medication to a user in response to a command from the processor based on the combination of said estimates, wherein the processor is a state estimator and is adapted to define a state vector for each model, the state vector comprising a set of variables each having an associated uncertainty, the set of variables including a variable representing an unexplained change in glucose level with each model having a different standard deviation in the unexplained change in glucose level;

wherein the first and second models each comprise a sub-model of glucose kinetics in the blood of said human or animal, a sub-model of interstitial glucose kinetics, a sub-model of insulin absorption, a sub-model of insulin action and a sub-model of gut absorption; and wherein the state vector includes the following states $$x_k = (q_{1f,k}, q_{2f,k}, u_{S,k}, F_k, q_{3f,k})^T$$

where $q_{1,f,k}$, $q_{2f,k}$, and $q_{3f,k}$ represent glucose amounts in the accessible, non-accessible and interstitial compartments excluding the contribution from meals, $u_{s,k}$ is the unexplained glucose influx and $F_k$ is glucose availability.

24. A method according to claim 23, comprising calculating said estimate of said inferred level using real time monitoring comprising:

inputting, to said processor, a time series of glucose level measurements from a sensor, said glucose level measurements being indicative of a inferred level of said glucose in a part of said human or animal, calculating, using said processor, a first estimate of said inferred glucose level from said measured glucose level using a first glucoregulatory system model, calculating, using said processor, a second estimate of said inferred glucose level from said measured substance level using a second glucoregulatory system model with said second system model being a variation of said first system model and predicting, using said processor, a combined estimate of the inferred glucose level based on a combination of the first and second estimates.

25. A method according to claim 15 or claim 23, further comprising displaying a suggested insulin bolus to be applied on a user interface, wherein the suggested insulin bolus is calculated by the processor as the amount of medication required to bring the combined estimate into line with a desired glucose value.

26. A non-transitory carrier carrying computer program code to, when running on said processor, implement the method of claim 15.

27. Apparatus according to claim 1, wherein the glucose kinetics sub-model is described as $$\frac{dq_1(t)}{dt} = -(S_{ID}x_D(t) + k_{21})q_1(t) + k_{12}q_2 - F_{01} + EGP(t) + Fu_A(t) + u_S(t)$$

$$\frac{dq_2(t)}{dt} = +k_{21}q_1(t) - k_{12}q_2(t)$$

$$g_P(t) = \frac{q_1(t)}{V_G}$$

where $q_1(t)$ and $q_2(t)$ are the masses of glucose in the accessible and non-accessible glucose compartments (mmol/kg), $k_{21}$ and $k_{12}$ are the fractional transfer rates (/min), $F_{01}$ is the non-insulin dependent glucose utilisation (mmol/kg/min), EGP(t) is the endogenous glucose production (mmol/kg/min), $S_{I,D}$ is peripheral insulin sensitivity (/min per mU/l), F is glucose bioavailability (unitless), $u_S(t)$ is unexplained glucose influx (mmol/kg/min), $g_P(t)$ is plasma glucose concentration, $V_G$ is the glucose distribution volume in the accessible compartment (l/kg).

28. Apparatus according to claim 1, wherein the interstitial glucose kinetics sub-model is described as $$\frac{dq_3(t)}{dt} = -k_{31}(q_3(t) - q_1(t))$$

$$g_{IG}(t) = \frac{q_3(t)}{V_G}$$

where $q_3(t)$ is the mass of glucose in the interstitial fluid (mmol/kg), $k_{31}$ is the fractional transfer rate (/min), and $g_{IG}(t)$ is interstitial glucose concentration.

29. Apparatus according to claim 1, wherein the state vector comprises a subset of the parameters of each model.

30. A method according to claim 15, wherein the insulin absorption sub-model is described by a two compartment model $$\frac{di_1(t)}{dt} = -\frac{1}{t_{xI}}i_1(t) + \frac{u(t)}{60} + \delta_{t_j}(t)v(t)$$

$$\frac{di_2(t)}{dt} = \frac{1}{t_{xI}}[i_2(t) - i_1(t)]$$

$$i(t) = \frac{1}{t_{xI}} \frac{1000}{MCR_I W} i_2(t)$$

where $i_1(t)$ and $i_2(t)$ is the amount of insulin in the two subcutaneous insulin depots (U), i(t) is the plasma insulin concentration (mU/l), u(t) denotes insulin infusion (U/h), v(t) denotes insulin boluses given at time $t_j$ (U), $t_{max,I}$ is the time-to-peak of insulin absorption (min), $MCR_I$ is the metabolic clearance rate of insulin (L/kg/min), and W is subject's weight (kg).

31. A method according to claim 15, wherein the insulin action sub-model is described as $$\frac{dr_D(t)}{dt} = p_{2D}(i(t) - r_D(t))$$

$$\frac{dr_E(t)}{dt} = p_{2E}(i(t) - r_E(t))$$

where $r_D$ and $r_{EGP}$ are the remote insulin actions affecting glucose disposal and endogenous glucose production, respectively, (mU/l), and $p_{2,D}$ and $p_{2,EGP}$ are the fractional disappearance rates associated with the remote insulin actions (/min).

32. A method according to claim 15, wherein the gut absorption sub-model is described by a two compartment model $$\frac{da_1(t)}{dt} = \frac{1}{t_{xG}}a_1(t) + v_G(t)$$

$$\frac{da_2(t)}{dt} = -\frac{1}{t_{xG}}[a_2(t) - a_1(t)]$$

$$u_A(t) = \frac{5.551}{Wt_{xG}}a_2(t)$$

where $a_1(t)$ and $a_2(t)$ is the amount of glucose in the two absorption compartments (g), $u_A(t)$ is the gut absorption rate (mmol/kg/min), $v_G(t)$ denotes meal ingestion (g/min), and $t_{max,G}$ is the time-to-peak of the gut absorption (min).

33. A method according to claim 15, wherein the state vector comprises a subset of the parameters of each model.

34. Apparatus according to claim 12, wherein the desired glucose value varies with time to define a trajectory of values.

* * * * *